(12) United States Patent
Everett et al.

(10) Patent No.: US 10,571,243 B2
(45) Date of Patent: Feb. 25, 2020

(54) SYSTEMS AND METHODS FOR IMPROVED OCT MEASUREMENTS

(71) Applicants: Carl Zeiss Meditec, Inc., Dublin, CA (US); Carl Zeiss Meditec AG, Jena (DE)

(72) Inventors: Matthew J. Everett, Livermore, CA (US); Tilman Schmoll, Dublin, CA (US); Nathan Shemonski, San Francisco, CA (US); Alexandre R. Tumlinson, San Leandro, CA (US)

(73) Assignees: CARL ZEISS MEDITEC, INC., Dublin, CA (US); CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 16/075,934

(22) PCT Filed: Feb. 10, 2017

(86) PCT No.: PCT/EP2017/053017
§ 371 (c)(1),
(2) Date: Aug. 6, 2018

(87) PCT Pub. No.: WO2017/137567
PCT Pub. Date: Aug. 17, 2017

(65) Prior Publication Data
US 2019/0056214 A1    Feb. 21, 2019

Related U.S. Application Data

(60) Provisional application No. 62/294,868, filed on Feb. 12, 2016.

(51) Int. Cl.
*G01B 9/02* (2006.01)
*A61B 3/10* (2006.01)
(Continued)

(52) U.S. Cl.
CPC .......... *G01B 9/02091* (2013.01); *A61B 3/102* (2013.01); *A61B 3/1225* (2013.01); (Continued)

(58) Field of Classification Search
CPC ............ G01B 9/02017; G01B 9/02027; G01B 9/02028; G01B 9/02087; G01B 9/02091
See application file for complete search history.

(56) References Cited

U.S. PATENT DOCUMENTS 7,061,622 B2    6/2006    Rollins et al.
9,046,339 B2    6/2015    Blatter et al.
(Continued)

FOREIGN PATENT DOCUMENTS

EP    2719324 A2    4/2014
WO    2015/189174 A2    12/2015

OTHER PUBLICATIONS

Adie et al., "Guide-Star-based Computational Adaptive Optics for Broadband Interferometric Tomography", Applied Physics Letters, vol. 101, 2012, pp. 221117-1-221117-5.
(Continued)

*Primary Examiner* — Jonathan M Hansen
(74) *Attorney, Agent, or Firm* — Morrison & Foerster LLP (57) ABSTRACT

Various systems and methods for sequential angle illumination to achieve ultra-high resolution optical coherence tomography (OCT) images. One example OCT system includes a light source, a beam divider, sample arm optics, a detector, and a processor. The light source generates a light beam to illuminate the sample. The beam divider separates the light beam into reference and sample arms. The sample arm optics sequentially illuminates a location in the sample with the light beam from different angles. The detector receives light returned from the reference arm and the
(Continued)

sample illuminated at each angle and generates signals. The processor combines the signals to generate an image, which has a transverse resolution that is higher than the transverse resolution achieved from the signal generated from a single angle.

17 Claims, 5 Drawing Sheets

(51) Int. Cl.
    *A61B 3/12*           (2006.01)
    *A61B 3/15*           (2006.01)

(52) U.S. Cl.
    CPC .......... *A61B 3/152* (2013.01); *G01B 9/02017* (2013.01); *G01B 9/02028* (2013.01); *G01B 9/02061* (2013.01); *G01B 9/02087* (2013.01)

(56) References Cited

U.S. PATENT DOCUMENTS

| | | | |
|---|---|---|---|
| 9,055,892 | B2 | 6/2015 | Narasimha-Iyer et al. |
| 2009/0066727 | A1 | 3/2009 | Lu et al. |
| 2013/0003076 | A1* | 1/2013 | Yoshida .................. A61B 3/102 356/479 |
| 2014/0028974 | A1 | 1/2014 | Tumlinson |
| 2014/0218684 | A1 | 8/2014 | Kumar et al. |
| 2014/0288418 | A1* | 9/2014 | Milner .................. A61B 5/0066 600/425 |
| 2015/0159992 | A1 | 6/2015 | Buckland et al. |
| 2015/0201833 | A1 | 7/2015 | Chong |

OTHER PUBLICATIONS

Boccara et al., "Full-field OCT: A Non-Invasive Tool for Diagnosis and Tissue Selection", SPIE Newsroom, 2013, pp. 1-4.
Bonin et al., "In Vivo Fourier-Domain Full-Field OCT of the Human Retina with 1.5 Million A-lines/s", Optics Letters, vol. 35, No. 20, Oct. 15, 2010, pp. 3432-3434.
Davis et al., "Interferometric Synthetic Aperture Microscopy: Computed Imaging for Scanned Coherent Microscopy", Sensors, vol. 8, Jun. 11, 2008, pp. 3903-3931.
Desjardins, "Angle-Resolved Optical Coherence Tomography with Sequential Angular Selectivity for Speckle Reduction", Optics Express, vol. 15, No. 10, May 14, 2007, pp. 6200-6209.
Fercher et al., "Optical Coherence Tomography—Principles and Applications", Reports on Progress in Physics, vol. 66, 2003, pp. 239-303.
Fercher, Adolf F., "Optical Coherence Tomography", Journal of Biomedical Optics, vol. 1, No. 2, Apr. 1996, pp. 157-173.
Gutzler et al., "Coherent Aperture-Synthesis, Wide-Field, High-Resolution Holographic Microscopy of Biological Tissue", Optics Letters, vol. 35, No. 8, Apr. 15, 2010, pp. 1136-1138.
Haindl et al., "Three-Beam Doppler Optical Coherence Tomography using a Facet Prism Telescope and MEMS Mirror for Improved Transversal Resolution", Journal of Modern Optics, vol. 62, No. 21, 2014, pp. 1-8.
Hillman et al., "Common Approach for Compensation of Axial Motion Artifacts in Swept-source OCT and Dispersion in Fourier-domain OCT", Optics Express, vol. 20, No. 6, Mar. 12, 2012, pp. 6761-6776.
Hillmann et al., "Efficient Holoscopy Image Reconstruction", Optics Express, vol. 20, No. 19, Sep. 10, 2012, pp. 21247-21263.
Hughes et al., "Speckle Noise Reduction in Optical Coherence Tomography of Paint Layers", Applied Optics, vol. 49, No. 1, Jan. 1, 2010, pp. 99-107.
International Preliminary Report on Patentability received for PCT Patent Application No. PCT/EP2017/053017, dated Aug. 23, 2018, 10 pages.
International Search Report and Written Opinion received for PCT Patent Application No. PCT/EP2017/053017, dated Apr. 24, 2017, 13 pages.
Izatt et al., "In Vivo Bidirectional Color Doppler Flow Imaging of Picoliter Blood Volumes using Optical Coherence Tomography", Optics Letters, vol. 22, No. 18, Sep. 15, 1997, pp. 1439-1441.
Jain et al., "Modified Full-Field Optical Coherence Tomography: A Novel Tool for Rapid Histology of Tissues", Journal of Pathology Informatics, vol. 2, No. 28, 2011, 9 pages.
Kak et al., "Principles of Computerized Tomographic Imaging", Society for Industrial and Applied Mathematics, 1988, 333 pages.
Klein et al., "Joint Aperture Detection for Speckle Reduction and Increased Collection Efficiency in Ophthalmic MHz OCT", Biomedical Optics Express, vol. 4, No. 4, Apr. 1, 2013, pp. 619-634.
Kumar et al., "Numerical Focusing Methods for Full Field OCT: A Comparison Based on a Common Signal Model", Optics Express, vol. 22, No. 13, Jun. 30, 2014, pp. 16061-16078.
Kumar et al., "Subaperture Correlation based Digital Adaptive Optics for Full Field Optical Coherence Tomography", Optics Express, vol. 21, No. 9, May 6, 2013, pp. 10850-10866.
Laubscher et al., "Video-Rate Three-Dimensional Optical Coherence Tomography", Optics Express, vol. 10, No. 9, May 6, 2002, pp. 429-435.
Liu et al., "Rapid Scanning All-Reflective Optical Delay Line for Real-Time Optical Coherence Tomography", Optics Letters, vol. 29, No. 1, Jan. 1, 2004, pp. 80-82.
Lujan et al., "Directional Optical Coherence Tomography Provides Accurate Outer Nuclear Layer and Henle Fiber Layer Measurements", Retina, vol. 35, No. 8, Aug. 2015, pp. 1511-1520.
Malmström, Mikael, "Multi-Angle Oblique Optical Coherence Tomography", Lunds Report on Atomic Physics—399, <Available Online at http://www.diva-portal.org/smash/get/diva2:488441/FULLTEXT01.pdf>, Sep. 29, 2008, 50 pages.
Nakamura et al., "Complex Numerical Processing for In-Focus Line-Field Spectral-Domain Optical Coherence Tomography", Japanese Journal of Applied Physics, vol. 46, No. 4A, 2007, pp. 1774-1778.
Považay et al., "Full-Field Time-Encoded Frequency-Domain Optical Coherence Tomography", Optics Express, vol. 14, No. 17, Aug. 21, 2006, pp. 7661-7669.
Ralston et al., "Interferometric Synthetic Aperture Microscopy", Nature Physics, vol. 3, Feb. 2007, pp. 129-134.
Ralston et al., "Inverse Scattering for High-Resolution Interferometric Microscopy", Optics Letters, vol. 31, No. 24, Dec. 15, 2006, pp. 3585-3587.
Shemonski et al., "Computational High-Resolution Optical Imaging of the Living Human Retina", Nature Photonics, vol. 9, Jun. 22, 2015, 16 pages.
Vertu et al., "Diffraction Microtomography with Sample Rotation: Influence of a Missing Apple Core in the Recorded Frequency Space", Central European Journal of Physics, vol. 7, No. 1, 2009, pp. 22-31.
Wolf, Emil, "Three-Dimensional Structure Determination of Semi-Transparent Objects from Holographic Data", Optics Communications, vol. 1, No. 4, Sep./Oct. 1969, pp. 153-156.

\* cited by examiner

SYSTEMS AND METHODS FOR IMPROVED OCT MEASUREMENTS

PRIORITY

The present application is a National Phase application under 35 U.S.C. § 371 of International Application No. PCT/EP2017/053017, filed Feb. 10, 2017, which claims priority to U.S. Provisional Application Ser. No. 62/294,868 filed Feb. 12, 2016, the contents of each of which are hereby incorporated by reference.

FIELD OF THE INVENTION

The present application relates to improvements to interferometric imaging systems. In particular, this application relates to systems and methods for sequential angle illumination to achieve ultra-high resolution optical coherence tomography (OCT) images over an extended focal depth while minimizing signal loss outside the focal region.

BACKGROUND

The trade-off between depth of focus and transverse resolution is fundamental to classic imaging systems. The primary solution with such classic systems has been to take multiple images while changing the focal plane to achieve high resolution in multiple planes. One good example of this is the confocal microscope, where the focus of the light is stepped in the axial direction to acquire a series of high resolution en-face images that are combined to create a 3D volume.

Recently, holoscopic systems have demonstrated the ability to generate depth invariant transverse resolution, where the resolution at all depths is equal to the resolution at the beam focus, by combining the angle diverse out-of-focus light from multiple adjacent acquisitions (see for example, swept source based full-field holoscopy system discussed in Hillmann, D. et al., Opt. Express 20, 21247-63, 2012, and swept source based line-field holoscopy system discussed in US Patent Publication No. 2014/0028974, each of which are hereby incorporated by reference). However, point scanning holoscopic systems have still been limited to the resolution given by the numerical aperture (NA) of the illumination beam and collection system. Here, the NA of the collection system is defined as the NA over which light returning to the collection system is collected and interferes with the reference light, generating signal. As an example, for a single mode fiber based OCT system, the collection system NA is the NA of the single mode fiber. Field illumination holoscopy systems have achieved resolutions beyond that given by the numerical aperture (NA) of the illumination beam by using a detector array to collect the light with a higher NA (see for example, PCT Publication No. WO 2015/189174, hereby incorporated by reference). However, this leads to a mismatch in the NA for illumination and collection, resulting in vignetting between the illumination and collection apertures outside the focal plane. Increased parallelization can reduce this vignetting, but the parallelization with current hardware reduces the scan speed for a single acquisition, leading to motion artifact issues.

The two approaches used previously for increasing the NA and therefore increasing the image resolution beyond that of the illumination beam have been: 1) simultaneously collecting light from the illumination region from multiple angles on different elements of the detector array, and 2) imaging the illumination area on to the detector array across multiple detectors so that sub-areas of the illumination region are resolved.

In both cases, the NA of the collection system in a field illumination OCT system was increased, creating a mismatch between illumination and collection NA, thus creating the vignetting issues as discussed above.

The importance of collecting angular diverse scattering information to achieve high transverse resolution in OCT is well recognized, and has been discussed in, for example, Fercher, A. F., et al. (2003) "Optical coherence tomography—principles and applications." Reports on Progress in Physics 66: 239-203. It has previously been demonstrated that, after sequentially acquiring a set of closely spaced A-scans, one can combine the out of focus angular diverse scattering information from adjacent scans to remove out-of-focus-blur, generating depth invariant transverse resolution, where the resolution over an extended depth of field is given by the resolution of a single beam at focus (see for example, Davis, B. J., et al. (2008). "Interferometric Synthetic Aperture Microscopy: Computed Imaging for Scanned Coherent Microscopy." Sensors (Basel) 8 (6): 3903-3931).

Sequential acquisition of OCT data at multiple angles has been described before, both for speckle reduction (see for example, Desjardins, A. E., et al. (2007). "Angle-resolved Optical Coherence Tomography with sequential angular selectivity for speckle reduction." OPTICS EXPRESS 15 (10): 6200) and measurement of angle dependent scattering (see for example, Lujan, B. J., et al. (2015). "Directional Optical Coherence Tomography Provides Accurate Outer Nuclear Layer and Henle Fiber Layer Measurements." Retina 35 (8): 1511-1520).

Simultaneous collection of multiple angles has been demonstrated for speckle reduction (see for example, Klein, T., et al. (2013). "Joint aperture detection for speckle reduction and increased collection efficiency in ophthalmic MHz OCT." Biomed Opt Express 4 (4): 619-634) with multiple fiber optic collectors. However, the collection of light at different angles from the illumination limited the overlap region between the beams (vignetting outside the focal plane), resulting in the need to realign the relative positions of the collection beams for different eyes. Simultaneous collection of multiple angles has also been used for improving transverse resolution in partial or full field systems with a larger number of detector elements, which can overcome the vignetting issues by illuminating a large field of view (see for example, Hillmann, D., et al. (2012). "Common approach for compensation of axial motion artifacts in swept-source OCT and dispersion in Fourier-domain OCT." Opt Express 20 (6): 6761-6776). However these systems have slow sweep speed due to the large number of acquisition channels, leading to motion artifacts as described in Hillmann.

Here, we present new techniques for OCT and holoscopy systems to achieve resolution beyond that given by the illumination beam or collection system through sequentially illuminating and imaging the sample at different angles. This allows high spatially invariant resolution while eliminating the vignetting issues of field illumination systems. While depth invariant resolution has been demonstrated previously, the potential to increase the imaging resolution of the system by sequentially scanning at different angles has not been recognized.

SUMMARY

Systems and methods discussed herein achieve resolution beyond that of the illumination beam(s) while avoiding vignetting effects. As has been discussed herein, sequential transverse scanning can provide the out of focus angular diverse scattering information necessary to generate depth invariant resolution. Here we recognize that by extending this to sequentially scanning a sample location at different angles, we can further increase the angular diverse scattering information, enabling higher transverse resolution than one given by a single scan beam. This concept is described in detail for point scanning OCT and holoscopy systems and multi-beam OCT and holoscopic systems, but could apply to field illumination OCT and holoscopy systems as well.

According to one aspect of the subject matter described in the present application, an optical coherence tomography (OCT) system includes a light source for generating a light beam to illuminate a sample; a beam divider for separating the light beam into reference and sample arms, wherein the sample arm contains the sample to be imaged; sample arm optics for sequentially illuminating a location in the sample with the light beam from different angles; a detector for receiving light returning from the reference arm and the sample illuminated at each angle and generating signals in response thereto; and a processor for coherently combining the signals from the different angles at each location to generate an image of the sample, said image having a transverse resolution that is higher than the transverse resolution achieved from the signal generated from a single angle illumination.

According to another aspect of the subject matter described in the present application, method for high resolution imaging of a sample with a multi-beam OCT system includes illuminating different locations in the sample through multiple sample arm beam paths using a light source; adjusting the multiple sample arm beam paths such that at least one of the previously illuminated sample locations is illuminated again by a different sample arm beam path incident on the sample location at a different angle; combining light returning from the sample and light from one or more reference beam paths at a plurality of beam combiners; collecting light from each combiner and generating signals in response thereto; combining the signals from the different angles at each location to generate an image of the sample, said image having a transverse resolution that is higher than the transverse resolution achieved from the signal generated from a single angle; and storing or displaying the image or a further analysis thereof.

The features described herein are not all-inclusive and many additional features will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

FIGS. 2a-d illustrate exemplary multi-beam OCT systems that can be used to practice the embodiments relating to illuminating a sample from different angles with multiple light beams.

FIGS. 3d and 3e illustrate one embodiment of sample arm optics 115 capable of adjusting the angle of the light beam on the sample as shown in FIG. 3c. FIG. 3d shows a corner cube positioned to image a location at one angle while

FIGS. 4a-c illustrate simultaneous illumination of three adjacent points in a sample from different angles with three light beams. In particular, FIGS. 4a and 4b display a side view and a top view of said illumination, respectively.

FIGS. 5a-c illustrate three different arrangements, positioning, and/or sizes of beams with respect to a focusing lens (e.g., eye lens). In particular.

DETAILED DESCRIPTION

All patent and non-patent references cited within this specification are herein incorporated by reference in their entirety to the same extent as if the disclosure of each individual patent and non-patient reference was specifically and individually indicated to be incorporated by reference in its entirely.

Included below are some terms that will be helpful in understanding the invention:

Interferometric system: A system in which electromagnetic waves are superimposed, in order to extract information about the waves. Typically a single beam of at least partially coherent light is split and directed into different paths. These paths are commonly called sample path and reference path, containing sample light and reference light. The difference in optical path length creates a phase difference between them, which results in constructive or destructive interference. The interference pattern can be further analyzed and processed to extract additional information. There are special cases of interferometric systems, e.g. common path interferometers, in which the sample light and reference light travel along a shared path.

OCT System: An interferometric imaging system that determines the scattering profile of a sample along the OCT beam by detecting the interference of light reflected from a sample and a reference beam creating a three-dimensional (3D) representation of the sample. Each scattering profile in the depth direction (z) is reconstructed into an axial scan, or A-scan. Cross-sectional images (B-scans), and by extension 3D volumes, are built up from many A-scans, with the OCT beam moved to a set of transverse (x and y) locations on the sample.

The axial resolution of an OCT system is inversely proportional to the spectral bandwidth of the employed light source. The lateral resolution is defined by the numerical aperture of the illumination and detection optics and generally decreases when moving away from the focal plane. OCT systems exist in time domain and frequency domain implementations, with the time domain implementation based on low coherence interferometry (LCI) and the frequency domain implementation based on diffraction tomography. OCT systems can be point-scanning, multi-beam or field systems.

Holoscopy: An interferometric frequency-domain computational imaging technique based on OCT that combines signals from multiple angles in order to reconstruct a 3D representation of a sample with spatially invariant resolution. If the angular information from a single point, line, or two-dimensional area acquisition is insufficient for successfully reconstructing said 3D representation of a sample, two or more adjacent acquisitions can be combined to reconstruct said 3D representation of a sample. Holoscopy systems can be point-scanning, multi-beam or field systems.

Spatially invariant resolution: A lateral resolution that is first order independent of the axial position of the optical focal plane. Optical aberrations and errors in the reconstruction may lead to a slight loss of resolution with depth. This stands in contrast to Gaussian optics where the lateral resolution decreases significantly when moving away from the focal plane.

Computational adaptive optics: The computational correction of aberrations with a higher order than defocus.

Point-scanning system: A confocal scanning system that transversely scans the sample with a small spot and detects the backscattered single spatial mode light from the spot. The detected light may be spectrally dispersed and/or split into two channels for balanced detection. Many points have to be acquired in order to capture a 2D image or 3D volume.

Parallel OCT system: An OCT system containing multiple parallel acquisition channels. This can take the form of either a multi-beam system or a field illumination system.

Multi-beam system: A system that transversely scans the sample with multiple confocal points in parallel. A multi-beam system typically employs a dedicated interferometer for each parallel acquisition channel. The backscattered sample light of each parallel acquisition channel is typically coupled into a dedicated single mode fiber for each parallel acquisition channel.

Field illumination system: An interferometric imaging system wherein the sample is illuminated with a contiguous field of light which is then detected with a spatially-resolved detector. This is in contrast to imaging systems which use a focused spot or multiple spatially-separated focused spots with a single detector for each spot. Examples of field illumination systems include line-field, partial-field and full-field systems.

Line-field system: A field illumination system that illuminates the sample with a line and detects backscattered light with a spatially resolved detector. Such systems typically allow capturing a B-scan without transverse scanning. In order to acquire an enface image or volume of the sample, the line has to be scanned across the sample in one transverse direction.

Partial-field system: A field illumination system that illuminates an area of the sample which is smaller than the desired field of view and detects the backscattered light with a spatially resolved detector. In order to acquire an enface image or volume of the entire desired field of view one requires transverse scanning in two dimensions. A partial field illumination could be for example, a spot created by a low numerical aperture (NA) beam, a line, or any two-dimensional area including but not limited to a broad-line, an elliptical, square or rectangular illumination.

Full-field system: A field illumination system that illuminates the entire field of view (FOV) of the sample at once and detects the backscattered light with a spatially resolved detector. In order to acquire an enface image or volume, no transverse scanning is required.

The present application describes sequentially scanning the same location on a sample with an OCT or holoscopic system with optical scan beams at different angles to increase the angular diverse scattering information, enabling depth invariant transverse resolution beyond that given by a single scan beam. The idea can apply to single beam, multi-beam, and even field illumination OCT and holoscopic systems as defined above.

Figure 1:
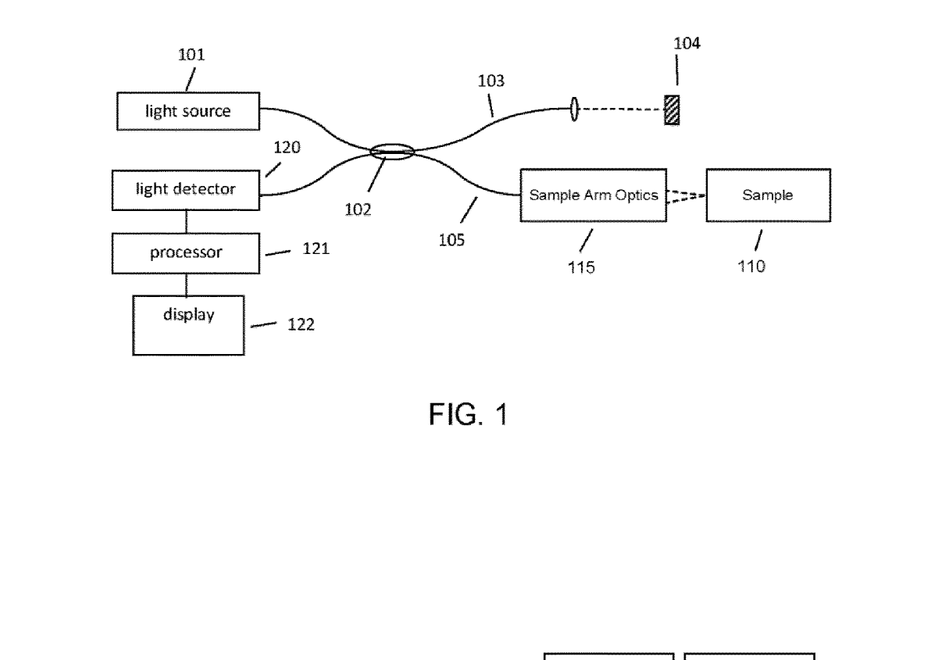
FIG. 1 illustrates an exemplary OCT system capable of practicing the embodiments relating to sequential illumination of a sample at different angles with a single light beam.

A generalized FD-OCT system that can be used to collect 3-D image data with illumination of the sample at a plurality of angles sequentially according to the present invention is illustrated in FIG. 1. The OCT system 100 includes a light source, 101, typical sources including but not limited to broadband light sources with short temporal coherence lengths in the case of SD-OCT or swept laser sources in the case of SS-OCT. A beam of light from source 101 is routed, typically by optical fiber 105, to illuminate the sample 110. Box 115 includes the optics responsible for delivering the light beam in the sample arm to the sample. Typical sample arm optics 115 include a beam collimating lens or lenses at the output of the fiber, a scanner between the output of the fiber and the sample, so that the beam of light is scanned laterally (in x and y) over the region of the sample to be imaged, and one or more focusing lenses.

Figure 3A:
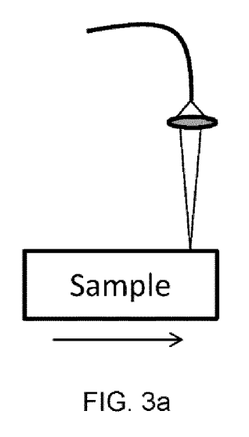
FIG. 3a shows scanning a point in the sample from a particular angle.
Figure 3B:
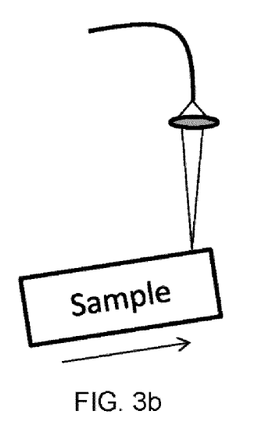
FIG. 3b shows an illustration where the sample is rotated and then rescanned providing illumination at a different angle and therefore increased angle diversity information at that location is collected.
Figure 3C:
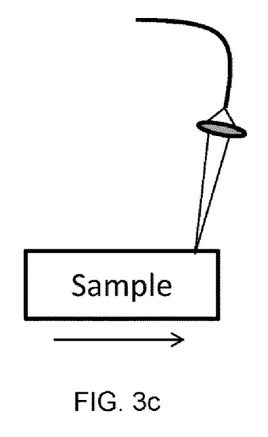
FIG. 3c illustrates an alternative way of achieving the increased angle diversity information by tilting the light beam to scan the same point in the sample from a different angle.

There are a plurality of ways to achieve sequential angle illumination of a location on the sample using the system in FIG. 1. The concept of sample or light beam adjustment to scan the sample at a different angle is illustrated generally with respect to FIGS. 3a-c. In FIG. 3a, a location on the tissue is scanned at a first angle. FIG. 3b illustrates how rotating the sample relative to the OCT beam allows for the same location on the sample to be rescanned, and therefore increased angle diversity information is collected. This could be achieved if the sample can be positioned on an adjustable stage and moved relative to the OCT system. This could be used for non-human or ex vivo samples, but can be challenging when the sample is in vivo, like when imaging the human eye. Alternatively, the OCT beam could be tilted relative to the sample as shown in FIG. 3c to obtain this angle diversity information. The tilt may be achieved by either moving the sample arm optics 115 relative to the sample 110 or moving one or more elements/components inside the sample arm optics 115 as shown for example in FIGS. 3d-g and discussed in detail below. Note that the relative tilting between the OCT beam and sample (by rotating either the beam or the sample) need not happen after a complete collection of a data set, but could occur after each A-scan, each B-scan, after any number of A-scans, or after any number of wavelengths.

Returning the description of FIG. 1, light scattered from a location on the sample illuminated at each angle is collected, typically into the same fiber 105 used to route the light for illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light from each angle is combined with reference light, typically in a fiber coupler 102, to form light interference in a detector 120. Although a single fiber port is shown going to the detector, those skilled in the art recognize that various designs of interferometers can be used for balanced or unbalanced detection of the interference signal. The detector 120 generates signals in response to light collected from different angles and supplies the generated signals to a processor 121 that combines the signals from the different angles coherently and generates an improved transverse resolution image of the sample. The coherent combining involves averaging or adding the complex signals or the interference fringe data. In one embodiment complex addition is performed by assuming the second beam is at an angle theta in the x direction relative to the first beam, then the complex value signal from the second beam would be multiplied by a phase ramp exp(ikx), where k=2pi sin(theta)/lambda, then added to the complex valued signal from the first beam. Additional embodiments will be discussed in further detail below. The image so generated has a transverse resolution corresponding to the angular spread between the two beams, which is larger than the NA of each beam, resulting in a higher transverse resolution than that achieved from the signal generated from scanning the sample at a single angle.

The results of the processing can be stored in the processor 121 or other storage medium or displayed on display 122. The processing and storing functions may be localized within the OCT instrument or functions may be performed on an external processing unit to which the collected data is transferred. This unit could be dedicated to data processing or perform other tasks which are quite general and not dedicated to the OCT device. The processor 121 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm typically have a tunable optical delay to generate interference. Balanced detection systems are often used in TD-OCT and SS-OCT systems, while spectrometers are used at the detection port for SD-OCT systems. The invention described herein could be applied to any type of OCT system. While it is described in detail for point and multi-point scanning systems, sequential angle scanning can be readily extended to field and partial field illumination OCT and holoscopic systems.

In Fourier Domain optical coherence tomography (FD-OCT), each measurement is the real-valued spectral interferogram ($S_j(k)$). The real-valued spectral data typically goes through several postprocessing steps including background subtraction, dispersion correction, etc. The Fourier transform of the processed interferogram, results in a complex valued OCT signal output $A_j(z)=|A_j|e^{i\varphi}$. The absolute value of this complex OCT signal, $|A_j|$, reveals the profile of scattering intensities at different path lengths, and therefore scattering as a function of depth (z-direction) in the sample. Similarly, the phase, $\varphi_j$ can also be extracted from the complex valued OCT signal. The profile of scattering as a function of depth at a single location is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube.

Figure 3D:
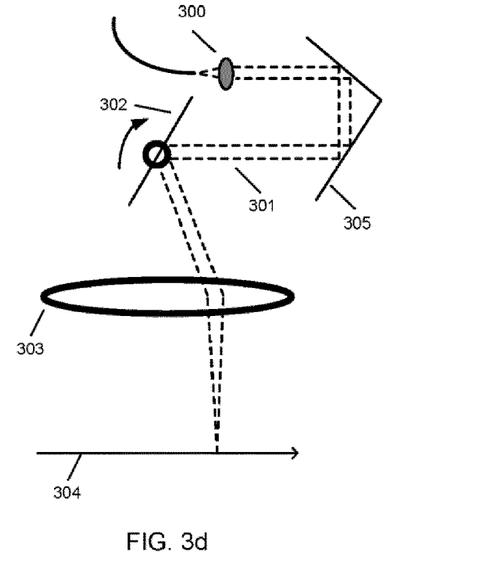
Figure 3E:
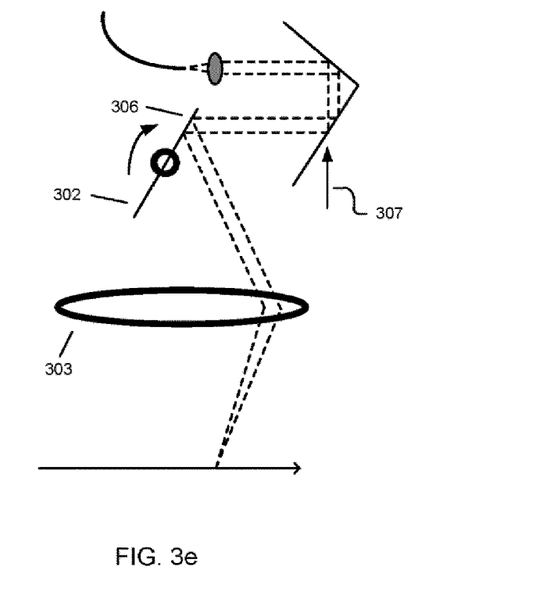
FIG. 3e shows the corner cube shifted resulting in the same location on the sample being imaged at a different angle.

One method of tilting the OCT beam relative to the sample would be to cause the beam to enter the focusing lens at a different location, as shown for example in FIGS. 3d and 3e. In this embodiment, the displacement or tilt in the OCT beam 301 is introduced with the use of a corner cube 305 and a pivoting mirror element 302. For instance, a motor may be connected to the cube 305 that moves the cube in up-down direction as indicated by arrow 307 causing the displacement or tilt in the light beam 301 so that it hits the mirror 302 at a different location 306 (see FIG. 3e), passing through lens 303 in a different location so that it focuses on the sample 304 at the same location, but from a different angle. In such an implementation, sample arm optics 115 of the OCT system 100 could include a collimating lens 300 at the output of the fiber, the corner cube 305, the rotating mirror element 302, and focusing lens 303. The corner cube could be placed before or after the scanning element.

Figure 3F:
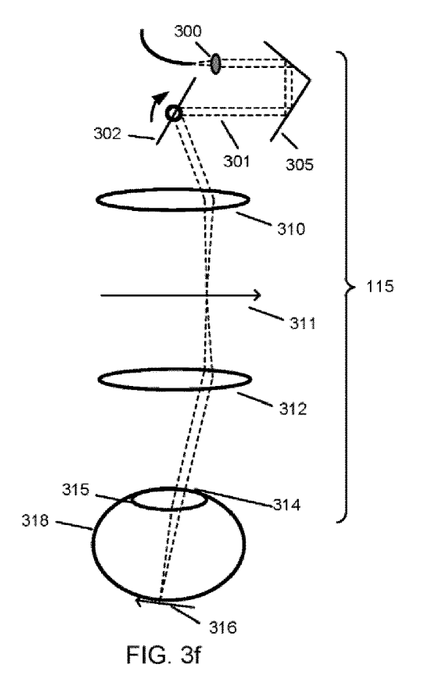
FIGS. 3f and 3g show the same sample arm optics arrangement as in FIGS. 3d and 3e but with additional optical components added when the sample is an eye.
Figure 3G:
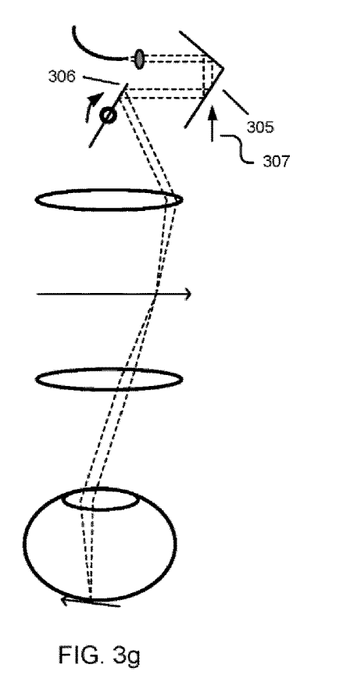

FIGS. 3f and 3g illustrate one embodiment of sample arm optics 115 for the case where the sample is a retina 310 of a human eye 318. Note that same reference numerals are used to refer to components already discussed above with respect to FIGS. 3d and 3e. For such an ophthalmic system to achieve sequential angle illumination, the light beam would be directed through a different entry point through the pupil 314. The system is designed such that the lens 315 of the eye 318 is part of the optical system responsible for focusing the beam of light 301 on the retina 310. The sample arm optics 115 illustrated in FIG. 3f are based on those discussed in reference to FIGS. 3d-e. They include a collimating lens 300 for collimating the beam from the fiber. A motorized corner cube beam reflector 305 is placed in the beam path in front of rotating mirror 302 which is placed optically conjugate to the pupil 314 of the eye. The corner cube could also be placed after the scanning mirror. A system of lenses 310 and 312 with adjustable airspace distance is typically used to compensate for various refractive errors present in the human population. An image conjugate to the retina surface (indicated by reference numeral 311) is shown internal to the system of lenses 310 and 312. As discussed above, laterally adjusting the position of the pupil of the eye relative to a scanning device is enough to introduce different scanning angles at the retina. FIG. 3g illustrates the beam path when the corner cube 305 is translated resulting in the beam hitting a different location 306 on scanning mirror 302 and thus passing through different locations on the lenses and eye pupil and illuminating the same location on the retina at a different angle.

A system which achieves the beam position change in the pupil by translating the beam across the scanning mirror will have the additional benefit that it may be faster to shift the beam across the rotating mirror, than it is to shift the entire optical assembly to acquire subsequent angle shifted scans. To prevent unintentional tilt of the sample, it may be further desirable to implement a simultaneous active or passive tracking to maintain the position of the optical system relative to the pupil of the eye.

In typical holoscopy systems, the detected light fields are sampled linearly in x and y as a function of optical wavenumber k, with $k=2\pi/\lambda$, for the case where one or more detectors (or a detector array) is placed at a conjugate plane of the sample, and linearly in kx and ky as a function of optical wavenumber k, for the case where a detector array is placed at a conjugate plane of the pupil. As mentioned earlier, the potential for sequential acquisition of different kx and/or ky locations had not been recognized, and therefore sampling the (kx; ky) space was done through parallel acquisition on a detector array. Here, we sample the (kx; ky)-space by illuminating and collecting light with light beams from different angles.

Once the different k's, are acquired, the image can be holoscopically reconstructed by following Wolf's approach of computationally reconstructing the three-dimensional distribution of the scattering potential of the object from the distribution of amplitude and phase of the light scattered by the object (Wolf, E. (1969). Three-dimensional structure determination of semi-transparent objects from holographic data. *Optics Communications*, 1 (4), 153-156). The so-called Fourier diffraction theorem, relates the Fourier transform of the acquired scattering data with the Fourier transform of the sample's structure. A correct, spatially invariant volume reconstruction by a 3D Fourier transform of the acquired scattering data is however only obtained if the acquired data kx and ky are sampled on a rectangular lattice {kx, ky, kz}. Holoscopy systems however generate spatial frequency domain samples over circular arcs (Kak, A. C. et al., Principles of Computerized Tomographic Imaging 1988): $k\_z=\sqrt{(k^2-k\_x^2-k\_y^2)}$. It is therefore desirable to apply an interpolation in the frequency domain in order to resample the acquired data from being sampled in {kx, ky, k} to be uniformly sampled in {kx, ky, kz} prior to the 3D Fourier transform. In optical coherence tomography, the resampling in the spatial frequency domain is skipped (see for example, Fercher, A. F. (1996). Optical coherence tomography. *Journal of Biomedical Optics*, 1 (2), 157-173). Not resampling the data in the spatial frequency domain to the proper lattice results in reconstructions with out of focus blurring.

Prior to the resampling step, the acquired data is transformed to the spatial frequency domain using a 2D Fourier transform (FT) along the transverse directions. For an efficient implementation of the FT one would likely make use of the fast Fourier transform (FFT), which is why we will from here on use the term FFT interchangeably with the term FT. Someone skilled in the art can further recognize that one may alternatively choose to use other transforms to transform signals between the spatial domain (or time domain) and the frequency domain, such as wavelet transforms, chirplet transforms, fractional Fourier transforms, etc. In the spatial frequency domain, the measured field at each optical frequency is then computationally propagated to the reference plane. Note that this step can be skipped in case the detector is placed at a conjugate plane of the sample and the optical path length difference between the focal position in the sample arm and the reference mirror is matched, i.e. the focal position corresponds to the zero-delay position. One then applies the above mentioned resampling in order to obtain data uniformly sampled in (kx, ky, kz). This now allows applying a 3D FFT to transform the data from the frequency domain to the spatial domain and therefore obtain a 3D representation of the sample's scattering potential with spatially invariant resolution.

Alternative reconstruction techniques, which can be used to obtain similar results were described for example by Ralston et al. (Ralston, T. S. et al., Opt. Lett. 31, 3585, 2006), Nakamura et al. (Nakamura, Y. et al., Jpn. J. Appl. Phys. 46, 1774-1778, 2007) and Kumar et al. (Kumar, A. et al., Opt. Express 21, 10850-66, 2013; Kumar, A. et al., Opt. Express 22, 16061-78, 2014) and US Patent Publication No. 2014/0218684.

In one embodiment of the present invention, a point scanning OCT system is used to collect a plurality of holoscopic data sets (as described in for example, Ralston, T. S. et al., Nature Physics 3, 129-134, 2007) where each data set is collected with a different relative angle between the OCT beam and the sample for each given point on the sample, as discussed above with respect to the OCT system in FIG. 1. Note that the specific order of data collection is not critical—one could collect holoscopic data sets with a shift in angle sequentially, or interleave the angle shifting, building up the holoscopic data sets in parallel. As the angle between the sample and OCT beams is changed, additional angle diverse scattering information is obtained. This increased angle diversity information can then be combined holoscopically to improve the transverse resolution of the imaging of the sample.

Wavefront aberrations and/or motion can make it more challenging to holoscopically reconstruct the data. The aberrations or motion can potentially be addressed by applying sub-aperture based aberration measurement and correction methods (see for example, US Publication No. 2014/0218684, hereby incorporated by reference). As each illumination angle enters the pupil at a different location as shown in FIGS. 3f and 3g, the sub-apertures described in the US Publication No. 2014/0218684 correspond to the illumination angles discussed herein. One can generate enface images from each of light beams illuminating the sample at the given incidence angles, and then measure the shifts between these enface images to determine the wavefront error introduced by the eye (and other system optics).

Once this wavefront error is determined, a corresponding phase correction can be added to the data from each acquisition angle so to eliminate the wavefront error, making the features in the enface images match. After the correction of the wavefront error, one coherently combines the signals by averaging all the channels, i.e. calculates the complex average of all channels in order to receive a single high resolution image. An example of an alternative method for a holoscopic combination of the angle diverse beams is to determine and correct the wavefront error of each beam individually and then average them coherently. An applicable method for the computational wavefront correction of single beams is for example described in Adie, S. G., et al. (2012). "Guide-star-based computational adaptive optics for broadband interferometric tomography." *Appl Phys Lett* 101 (22): 221117; and Shemonski, N. D., et al. (2015). "Computational high-resolution optical imaging of the living human retina." *Nature Photonics* 9 (7): 440-443. If only minimal wavefront aberrations are present or if aberration correction is not desired, one may coherently average the angle diverse beams directly to generate an image with a resolution limited by the present wavefront error.

The sequential angle concept can also be applied in multi-beam OCT and holoscopic systems. FIGS. 2a-d illustrate several exemplary multi-beam OCT systems for illuminating locations on a sample from different angles with multiple light beams. In particular, FIG. 2a displays a multi-beam OCT system that generates a sample image based on two sample and reference beam paths. Although it should be understood that this is just for example purposes and sampling based on more than two sample and reference beam paths is also possible and within the scope of the present disclosure. FIG. 2b shows another variation of a multi-beam OCT system that generates the improved transverse sample image based on splitting the light beam into two sample arm beam paths but only one reference arm beam path. FIG. 2c illustrates a multi-beam OCT system with three sample and reference arm channels or beam paths that interrogate the sample at three different locations. FIG. 2d shows a multi-beam OCT system with an optical switch for switching between three sample arm channels directed towards the same location on the sample to allow for sequential angle scanning without motion of any optical components in the sample arm. Each of the multi-beam OCT systems in FIGS. 2a-d is now discussed in detail below. It should be noted that same reference numerals are used in the later FIGS. 2b-d to refer to elements already discussed in reference to FIG. 2a and therefore the description of these elements will not be repeated or discussed in detail.

Figure 2A:
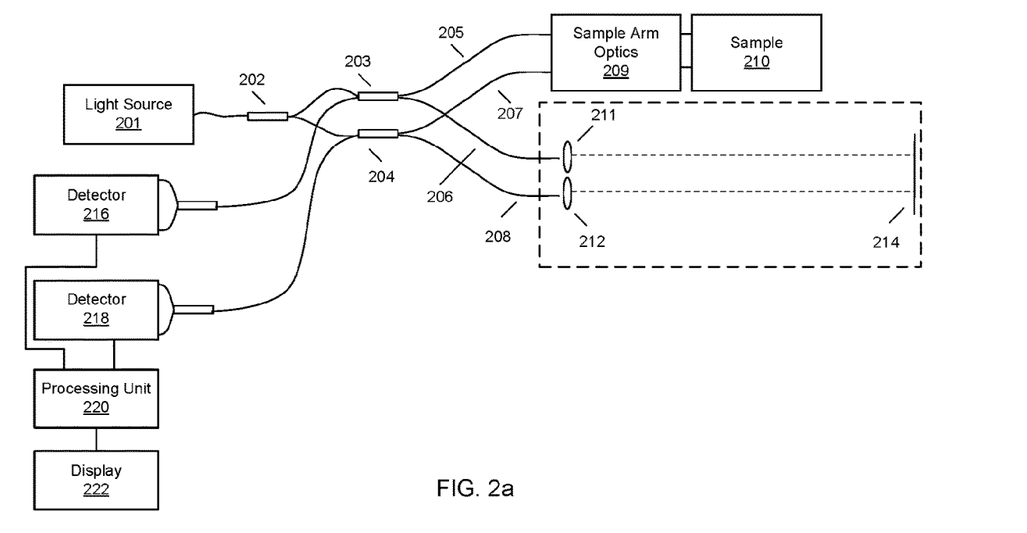
FIG. 2a displays a multi-beam OCT system that generates a sample image based on two sample and reference beam paths. Although it should be understood that this is just for example purposes and sampling based on more than two sample and reference beam paths is also possible and within the scope of the present disclosure.
Figure 2B:
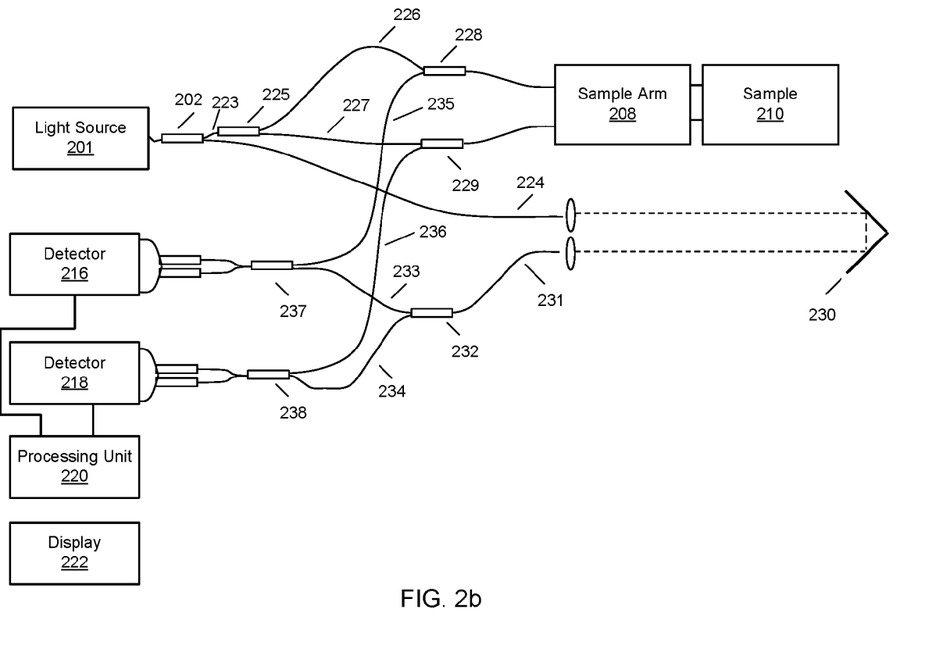
FIG. 2b shows another variation of a multi-beam OCT system that generates the improved transverse sample image based on splitting the light beam into two sample arm beam paths but only one reference arm beam path.
Figure 2C:
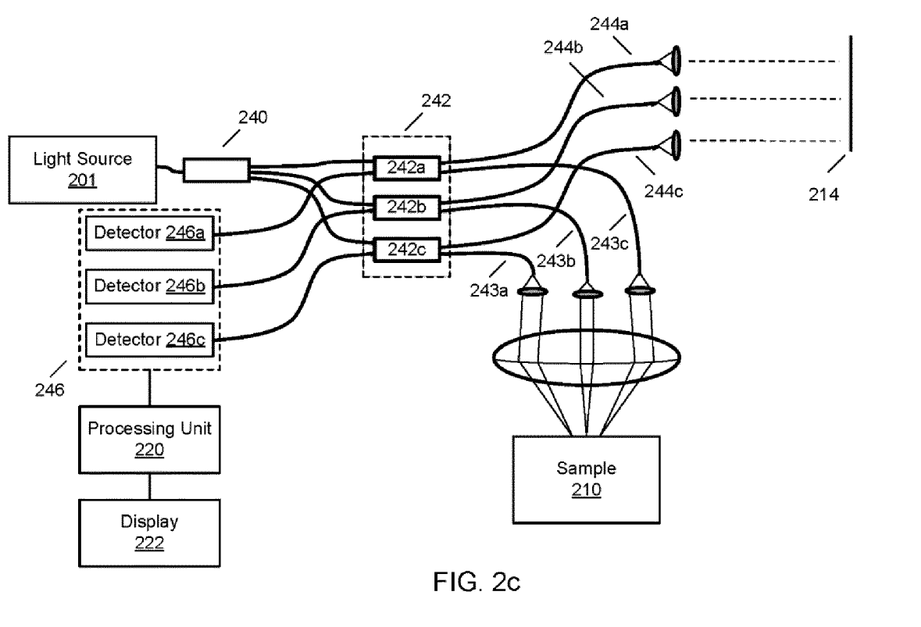
FIG. 2c illustrates a multi-beam OCT system with three sample and reference arm channels or beam paths that interrogate the sample at three different locations.
Figure 2D:
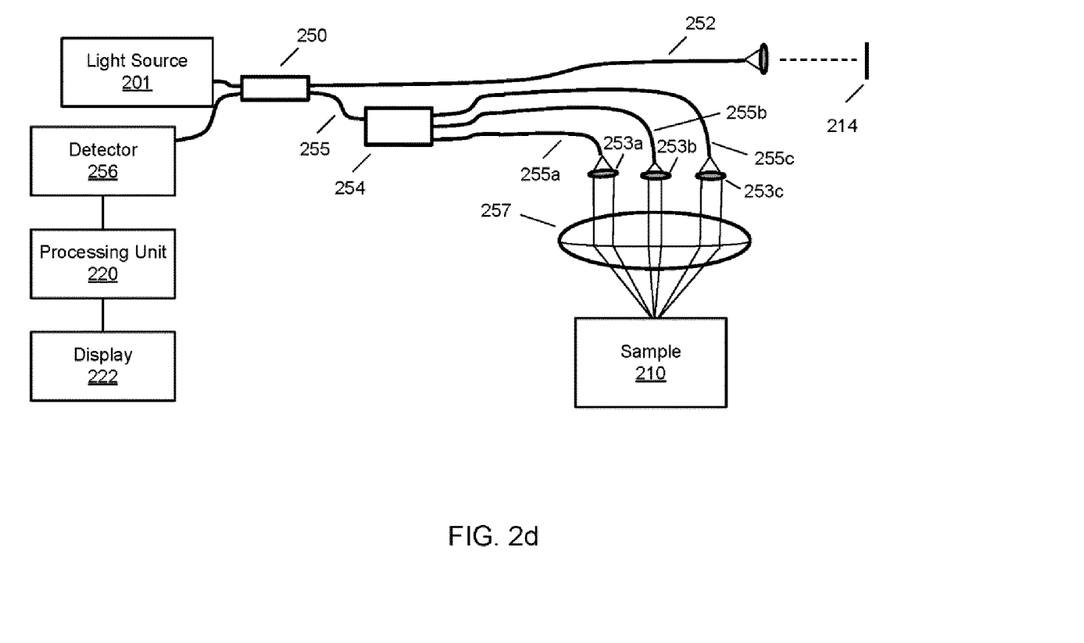
FIG. 2d shows a multi-beam OCT system with an optical switch for switching between three sample arm channels directed towards the same location on the sample to allow for sequential angle scanning without motion of any optical components in the sample arm.

FIG. 2a illustrates a multi-beam OCT system for sequentially illuminating a sample at different angles with two sample arm and reference arm light beam paths. A light source 201 generates a light beam to illuminate a sample 210, a typical sample being tissues in the human eye. Light splitter 202 splits the light produced by the light source 201 into two light paths, one which goes into a first fiber splitter 203 and another goes into a second fiber splitter 204. Instead of a single source and splitter 202, two separate sources could be used. The first fiber splitter 203 splits the received light into a first sample arm beam path 205 and a first reference arm beam path 206. The second fiber splitter 204 splits the received light into a second sample arm beam path 207 and a second reference arm beam path 208. The two sample arm beam paths 205 and 207 are directed toward sample arm optics 209 that illuminate the sample 210 (e.g., eye) at two different locations. The two beams are shifted relative to the sample either by translation of the sample or via one or more scanning elements in the sample arm optics such that the second beam illuminates a location previously illuminated by the first beam at a different relative angle between the beam and sample. In some embodiments, the sample arm optics 209 include optics that cause the tilt or displacement in the light paths so that they illuminate the pupil of the eye at two different angles. For instance, the sample arm 209 could include optics 115 as shown in FIG. 3f and discussed in reference to FIG. 1. Alternatively, the transverse scanning of the beams could achieve the sequential angle scanning.

Light scattered from the sample 210 illuminated at each location at multiple angles is collected, typically into the same sample arm fibers 205 and 207 that were used to route the light for illumination. Reference light derived from the first splitter 203 and the second splitter 204 travels a separate path, in this case involving fibers 206 and 208, and a retro-reflector 214 with an adjustable optical delay. In some instances, two retro-reflectors may be used for each reference arm beam path. Sample light 205 collected from the first location is combined with corresponding reference light 206, typically in the same fiber splitter 203, to form interference in a first detector 216. Sample light 207 collected from the second location is combined with corresponding reference light 208, typically in the same fiber splitter 204, to form light interference in a second detector 218. The detectors 216 and 218 generate signals in response to light collected from the two locations and supply the generated signals to a processing unit 220. The imaging process is repeated so that each location of interest is scanned by at least two different angles. The processor 220 then combines the signals from the multiple locations and angles and generates an improved transverse resolution image of the sample as described above. The image so generated has a transverse resolution higher than the transverse resolution typically achieved from the signal generated from scanning the sample at a single angle. The results of the processing can be stored in the processing unit 220 or other storage medium or displayed on display 222.

FIG. 2b illustrates another variation of a multi-beam OCT system for sequentially illuminating a sample at different angles with two light beam paths. The light splitter 202 here splits the light produced by the light source 201 into a sample light beam path 223 and a reference light beam path 224. The sample light beam path 223 is again split into two beam paths 226 and 227 by a splitter 225. The two sample light beams paths 226 and 227 are routed by optical fiber couplers 228 and 229, respectively, to illuminate the sample 210 at two different locations via the sample arm optics 208 as discussed elsewhere herein. The two sample arm beams are then adjusted (scanned) so that at least one of the beams illuminates a previously illuminated location on the sample at a different angle. This scanning is repeated until all of the desired locations have been illuminated by at least two different angles.

Light scattered from the locations on the sample 210 illuminated at each angle is collected, typically into the same fiber couplers 228 and 229 that were used to route the light for illumination. Reference light beam path 224 derived from the splitter 202 travels a separate path, in this case involving a reference mirror 230. Reference light returning from the mirror 230 (indicated by reference numeral 231) is then split by a fiber splitter 232 to form a first reference light path 233 and a second reference light path 234. Sample light collected from the first location (indicated by reference numeral 235) is combined with the first reference light path 233 in a fiber coupler 237, to form light interference in the first detector 216. Sample light collected from the second location (indicated by reference numeral 236) is combined with the second reference light path 234 in a fiber coupler 238 to form light interference in the second detector 218. In this figure detectors 216 and 218 are balanced detectors where the interference signal is split into two paths prior to entering the detector. The sample light beams are then moved relative to the sample to illuminate locations on the sample at different angles. The detectors 216 and 218 generate signals in response to light collected from the multiple locations and angles and supplies the generated signals to a processing unit 220 that combines the signals from the multiple locations and angles and generates an improved transverse resolution image of the sample.

Figures 4A, 4B:
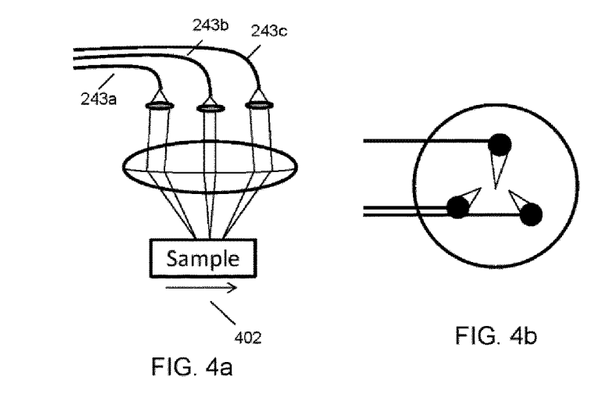
Figure 4C:
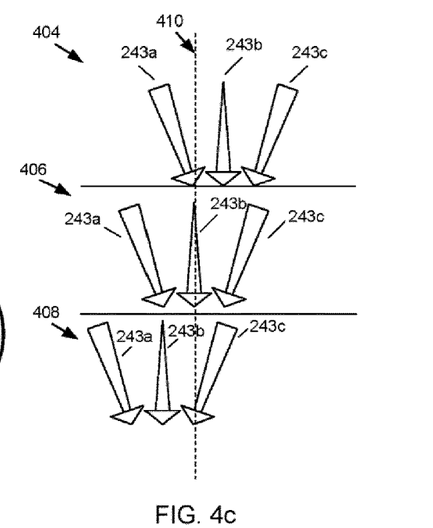
FIG. 4c shows how the three beams sequentially illuminate the same location on the sample at different angles as the location of the beams on the sample is shifted either via motion of the sample or the beams.

FIG. 2c illustrates an example of a multi-beam OCT system that illuminates three different locations on the sample 210 with three lights beams to achieve sequential angle illumination. The light source 201 produces a light beam that is split into three by a splitter 240. The three light beams are split into three (sample, reference) beampath pairs (243a, 244a), (243b,244b), and (243c, 244c) by splitters 242a, 242b, 242c, respectively. The three sample arm beam paths 243a-c simultaneously illuminate three different locations on the sample 210 (e.g., eye) from three different angles as shown in the figure. FIGS. 4a-c illustrate one embodiment of how this system can illuminate the locations at different angles sequentially FIGS. 4a and 4b display a side view and top view of the three beams, respectively, showing them entering the sample at different angles at three adjacent locations on the sample. FIG. 4c shows how the three beams sequentially interrogate the same point (indicated by line 410) on the sample at different angles as the beams are scanned across the sample or when the sample is moved relative to the instrument. This would be achieved by either a translation stage on the sample or by a scanning element in the sample arm optics. The top part of FIG. 4c indicated by arrow 404 shows the initial illumination condition where beam 243a images a point on the sample referenced by line 410. When the sample is moved to the right (or the beams are moved to the left) (indicated by the arrow 402 in FIG. 4a), in the second illumination condition (indicated by reference numeral 406), the beam 243b scans the same point from a different angle which was previously scanned by the beam 243a in the initial illumination. As the sample (or light beams) move farther, in the third illumination condition (indicated by arrow 408), the beam 243c scans the same location on the sample from a different angle than which was earlier scanned by beam 243a or 243b. In this design, each beam and corresponding acquisition channel would typically employ a dedicated interferometer, and for a fiber optic system, a dedicated single mode fiber (i.e., fibers 243a, 243b, and 243c) for illumination and collection.

Returning back to FIG. 2c, light scattered from the sample 210 illuminated at each location and angle is collected, typically into the same fiber splitters/couplers 242a-c that were used to route the light for illumination. Reference light derived from the splitters 242a-c travels a separate path, in this case involving fibers 244a-c and the retro-reflector 214 with an adjustable optical delay. Sample light 243a collected from the first location and angle is combined with corresponding reference light 244a, typically in the same fiber splitter 242a, to form light interference in a first detector 246a. Sample light 243b collected from the second location and angle is combined with corresponding reference light 244b, typically in the same fiber splitter 242b, to form light interference in a second detector 246b. Sample light 243c collected from the third location and angle is combined with corresponding reference light 244c, typically in the same fiber splitter 242c, to form light interference in a third detector 246c. The beams are then translated relative to the sample so that each location of interest is sampled by a different beam at a different angle. The detectors 246a-c generate signals in response to light collected from the three locations at multiple angles and supplies the generated signals to the processing unit 220. The processing unit 220 then coherently combines the signals from the three angles at each location to generate an improved transverse resolution image of the sample.

FIG. 2d illustrates another variation of a multi-beam OCT system that sequentially illuminates a single location on the sample 210 with three lights beams at three different angles using an optical switch 254. This is similar to the embodiments described in reference to FIG. 1. Here sample optics 115 would include the optical switch 254 and three beam paths 255a, 255b,255c, collimating lenses 253a-c, and lens 257, but, it would not be necessary to move the sample or optics to achieve the sequential angle illumination, this would be achieved by activating the different beam paths using the optical switch. The reason for illuminating the region of tissue sequentially with different angles rather than illuminating with all angles on the same tissue region simultaneously is two-fold. First, illuminating the same region with multiple beams simultaneously would increase the instantaneous intensity of the light on the tissue, increasing the potential for tissue damage. Second, if the multiple beams illuminate and collect light from the same regions simultaneously, then there will be cross-talk between the beams potentially leading to coherent interference of the light in the tissue, and unwanted light coupling between the channels back into the detection system.

As depicted, the light source 201 produces a light beam that is split into a reference arm beam path 252 and sample arm beam path 255 by a splitter 250. The sample arm beam path contains and is controlled by an optical switch 254 so that it sequentially illuminates a same point on the sample 210 from a particular angle dependent on which beam is active based on the optical switch. For instance, the optical switch 254 illuminates a point on the sample 210 first with the sample arm beam path 255a, second with the sample beam path 255b, and third with the sample beam path 255c. Light scattered from the sample 210 illuminated from each angle is collected and combined with the reference arm beam path 252, typically in the same fiber splitter 250, to form light interference in a detector 256. The detector 256 generates signals in response to light collected from each angle and supplies the generated signals to the processing unit 220 that combines the signals from the three angles coherently and generates an improved transverse resolution image of the sample.

For scanning of live samples such as the eye, motion of the tissue during data acquisition is a potential issue. In the ophthalmic case, motion of the head could lead to shifting of entry location in the pupil, and rotation of the eye can affect the incident location on the retina. Therefore one may wish to track either the pupil or retina or both, and either adjust the scanning beam to account for the motion, or correct the data post-acquisition to account for this.

Better imaging quality tends to be achieved at imaging depths a small distance away from the zero delay position between reference and sample arms where modulation frequency is relatively modest. When changing the angle of the scan, care should be taken with regard to the position of the object of interest relative to the reference surface. It is possible to acquire OCT from multiple angles without compromising the image depth of each acquisition. As illustrated in FIGS. 3a-c and 4a-c, in systems where scanning is achieved by translation of the sample relative to the optical system, the imaging depth of the sample can be kept relatively constant avoiding any roll-off effects introduced by large path length differences between the sample and reference.

Figures 5A, 5B, 5C:
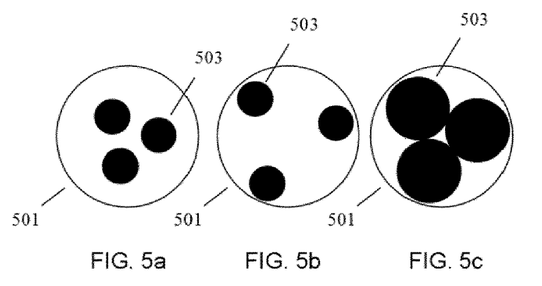
FIG. 5a shows an arrangement where three small beams are positioned close together on the lens allowing for dense sampling of angular information with low signal degradation.
FIG. 5b shows three small beams separated across the entire lens allowing for high transverse resolution with low signal degradation but sparse angular sampling.
FIG. 5c shows three large beams that provide high transverse resolution but high signal degradation.

Tradeoffs exist regarding the positioning and sizes of the beams in the pupil plane. Besides physical constraints, limitations related to the transverse point spread function (PSF) shape, resolution, collection efficiency, etc. exist. Although any number of configurations and number of beams can be imagined by one skilled in the art, three specific examples are provided in FIGS. 5a-c for a three beam system illuminating the tissue with light beams entering from three different illumination angles. These three different illumination angles could either be supported by a single channel OCT system illuminating each angle/beam sequentially, or a 3 channel OCT system, where all three angles are illuminated in parallel, but at different locations on the tissue as shown in FIG. 4b. In the FIGS. 5a-c, reference numeral 501 represents the focusing lens of a system (e.g. the lens of the eye) or a location near a Fourier plane of the sample, and reference numeral 503 represents a single illumination beam. In FIG. 5a, three small beams are positioned close together on the focusing lens. This allows for dense sampling of angular information with low signal degradation away from each individual focus. The drawback is the moderate achievable transverse resolution. FIG. 5b depicts an example where the small beams are separated across the entire focusing lens allowing for high transverse resolution with low signal degradation away from the focus, but sparse angular sampling. The sparse sampling of angles will lead to non-ideal PSF shapes (see for example, Gutzler T., Optics Letters, 35, 1136-1138, 2010). Finally, FIG. 5c provides high transverse resolution, good PSF shape, but high signal degradation away from each individual focus. Note that although three acquisition angles have been used in this example, any number of two or more angles could be used.

With reference to FIGS. 3d-3e, OCT systems typically utilize beam scanning such as that achieved with one or more rotating mirror elements 302. In traditional operation, when the beam 301 is centered at the pivot of the mirror 302 which lies on the optical axis of the scan lens 303, the sample beam forms an approximate normal to a surface of constant optical path length 304. Changing the angle of the beam incidence on the object can cause an apparent tilt of the reconstructed object within the imaging window. It is possible to use this tilt to accurately measure the angle at which the beam was incident on the sample, and thus use this measurement to assist in the high-resolution image reconstruction (determining the offset in the spatial-frequency domain) as discussed herein. It might be desirable to mitigate this tilt since, when scanning over a large field of view, a tilt relative to the zero delay may cause the object to move out of the usable imaging window. In such a case it may be advantageous to introduce an additional phase modulator into the system to counteract this apparent tilt of the sample.

Figure 6:
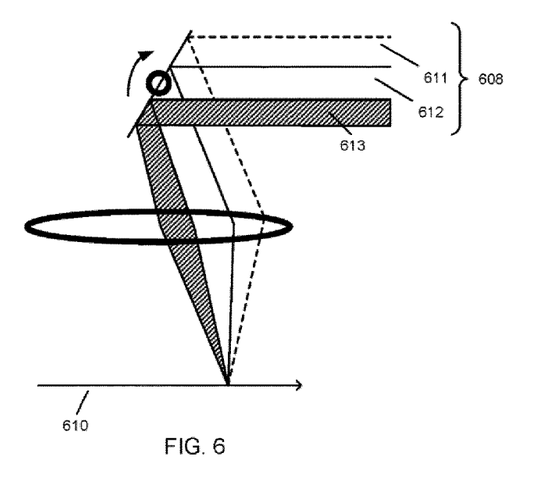
FIG. 6 shows an example illustration to demonstrate that the zero delay reference surface will be the same for all beam angles as was achieved for the beam angle corresponding to the beam placement on the center of the rotating mirror in FIG. 3d.

A phase modulator can take the form of a rapid scanning optical delay (RSOD), (e.g. Xiumei Liu, et al., "Rapid scanning all-reflective optical delay line for real-time optical coherence tomography," Opt. Lett. 29, 80-82 (2004)) to actively compensate for the apparent tilt. In the case of beam scanning by a rotating mirror which is later focused on a sample by a system of lenses, one simple way to compensate for the apparent tilt of the sample is to translate the beam away from the pivot point of the mirror (as shown by reference numeral 306 in FIG. 3e). If the beam is translated away from the pivot point of the scanning mirror, the beam angle at the object will shift, and a phase shift will be introduced to the beam as it is translated across the object so that the zero delay reference surface will be the same for all beam angles as was achieved for the beam angle corresponding to beam placement on the center of the rotating mirror. A simple way to think about this is to imagine a large beam (indicated by reference numeral 608 in FIG. 6) filling the rotating mirror coming to a focus at the object. In the absence of aberration, the entire large beam has the same path length at the focal plane, and this forms a single surface 610 (FIG. 6) as the beam scans across the object. The large beam can be decomposed into a number of smaller sub beams (611, 612, 613). Offset sub beams (611, 613) have zero delay depth at the same location as the central sub beam (612) which is equivalent to the configuration in FIG. 3d.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiment(s) of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof.

The invention claimed is:

1. An optical coherence tomography (OCT) system comprising:
   a light source for generating a light beam to illuminate a sample;
   a beam divider for separating the light beam into reference and sample arms, wherein the sample arm contains the sample to be imaged;
   sample arm optics for sequentially illuminating a location in the sample with the light beam from different angles;
   a detector for receiving light returning from the reference arm and the sample illuminated at each angle and generating signals in response thereto;
   a processor for coherently combining the signals from the different angles to generate an image of the sample, said image having a transverse resolution that is higher than the transverse resolution achieved from the signal generated from a single angle and wherein the coherently combining involves averaging or adding complex OCT data from the different angles.

2. The OCT system as recited in claim 1, wherein the sample is an eye.

3. The OCT system as recited in claim 1, wherein the sample arm optics comprise a splitter for dividing the light beam into multiple imaging beams and an optical switch, wherein sequential illumination of the sample at different angles is achieved with the optical switch.

4. The OCT system as recited in claim 3, wherein an imaging beam from the multiple imaging beams illuminates a point on the sample.

5. The OCT system as recited in claim 3, wherein an imaging beam from the multiple imaging beams illuminates a line on the sample.

6. The OCT system as recited in claim 1, wherein the OCT system is a holoscopic system.

7. The OCT system as recited in claim 1, wherein the sample arm optics include a corner cube reflector and a pivoting mirror element, wherein the sequential angle illumination is achieved by moving the beam on the pivoting mirror element using the corner cube reflector.

8. The OCT system as recited in claim 1, wherein an optical phase adjustment is applied between the sample arm and the reference arm to compensate for an apparent tilt introduced by different scanning angles.

9. The OCT system as recited in claim 1, further comprising an optical phase shifting element between the sample arm and the reference arm to compensate for an apparent tilt introduced by different scanning angles.

10. A method for high resolution imaging of a sample with a multi-beam optical coherence tomography (OCT) system, said method comprising:

illuminating different locations in the sample through multiple sample arm beam paths using a light source;

adjusting the multiple sample arm beam paths such that at least one of the previously illuminated sample locations is illuminated again by a different sample arm beam path incident on the sample location at a different angle;

combining light returning from the sample and light from one or more reference beam paths at a plurality of beam combiners;

collecting light from each combiner and generating signals in response thereto;

coherently combining the signals from the different angles at each location to generate an image of the sample, said image having a transverse resolution that is higher than the transverse resolution achieved from the signal generated from a single angle, wherein the coherently combining involves averaging or adding complex OCT signals from the different angles;

storing or displaying the image or a further analysis thereof.

11. The method as recited in claim 10, wherein the sample is an eye.

12. The method as recited in claim 10, wherein there are two sample arm beam paths and two reference beam paths.

13. The method as recited in claim 10, wherein there are three sample arm beam paths.

14. The method as recited in claim 10, wherein the adjusting step is achieved by moving the sample relative to the multi-beam OCT system.

15. The method as recited in claim 10, wherein the adjusting step is achieved by changing the location of the sample arm beam path on a scanning element positioned in the beam path.

16. The method as recited in claim 10, wherein the combining of each of the sample and reference arm beam path pairs determines an angular distribution of the scattering.

17. The method as recited in claim 10, wherein, prior to combining the sample and reference arm beam paths, shifting of the phase of the data from one or more sample arm beam paths is performed to correct for optical aberrations.

* * * * *

UNITED STATES PATENT AND TRADEMARK OFFICE
CERTIFICATE OF CORRECTION

PATENT NO. : 10,571,243 B2
APPLICATION NO. : 16/075934
DATED : February 25, 2020
INVENTOR(S) : Matthew J. Everett et al.

Page 1 of 1

It is certified that error appears in the above-identified patent and that said Letters Patent is hereby corrected as shown below:

In the Specification

In Column 13, Line 67, delete "255b,255c," and insert -- 255b, 255c, --, therefor.

Signed and Sealed this
Eighteenth Day of August, 2020

Andrei Iancu
*Director of the United States Patent and Trademark Office*